(12) United States Patent
Hattori

(10) Patent No.: US 7,790,007 B2
(45) Date of Patent: Sep. 7, 2010

(54) ELECTROPHORESIS CHIP, ELECTROPHORESIS APPARATUS, AND METHOD FOR ANALYZING A SAMPLE

(75) Inventor: Wataru Hattori, Tokyo (JP)

(73) Assignee: NEC Corporation, Tokyo (JP)

( * ) Notice: Subject to any disclaimer, the term of this patent is extended or adjusted under 35 U.S.C. 154(b) by 63 days.

(21) Appl. No.: 12/094,359

(22) PCT Filed: Nov. 17, 2006

(86) PCT No.: PCT/JP2006/322945

§ 371 (c)(1),
(2), (4) Date: May 20, 2008

(87) PCT Pub. No.: WO2007/063719

PCT Pub. Date: Jun. 7, 2007

(65) Prior Publication Data
US 2009/0045057 A1    Feb. 19, 2009

(30) Foreign Application Priority Data
Nov. 29, 2005    (JP)    ............... 2005-344466

(51) Int. Cl.
*G01N 27/447*    (2006.01)
*G01N 27/453*    (2006.01)
(52) U.S. Cl. ........................... 204/451; 204/601
(58) Field of Classification Search ......... 204/601–605, 204/451–455; 422/99, 100
See application file for complete search history.

(56) References Cited

U.S. PATENT DOCUMENTS

| | | | | |
|---|---|---|---|---|
| 6,264,892 | B1 * | 7/2001 | Kaltenbach et al. | 422/68.1 |
| 6,685,810 | B2 * | 2/2004 | Noca et al. | 204/450 |
| 6,726,820 | B1 * | 4/2004 | Frazier | 204/451 |
| 7,033,476 | B2 * | 4/2006 | Lee et al. | 204/603 |
| 2005/0139470 | A1 * | 6/2005 | Sze | 204/548 |

FOREIGN PATENT DOCUMENTS

| | | | |
|---|---|---|---|
| JP | 59-65245 A | | 4/1984 |
| JP | 60154150 A | * | 8/1985 |
| JP | 06-138089 A | | 5/1994 |
| JP | 2002-286696 A | | 10/2002 |
| JP | 2002-310858 A | | 10/2002 |
| JP | 2005-233944 A | | 9/2005 |

(Continued)

OTHER PUBLICATIONS

JPO English language abstract of Yoshida et al. JP 60154150 A, patent published on Aug. 13, 1985.*

(Continued)

*Primary Examiner*—Alex Noguerola
(74) *Attorney, Agent, or Firm*—Sughrue Mion, PLLC

(57) ABSTRACT

A sample which contains protein is stably maintained in a liquid state during electrophoresis. Electrophoresis chip 1 includes substrate 2, channels 5a to 5d which is provided on surface 3 of substrate 2 and which has openings 4a to 4d at the top thereof, wherein a sample solvent is adapted to be supplied to the channel, and evaporation inhibitor reservoirs 8a, 8b for storing an evaporation inhibitor for the sample solvent, the reservoir being provided independently of channel 5a to 5d and being spatially connected to opening 4a to 4d of channel 5a to 5d.

9 Claims, 4 Drawing Sheets

FOREIGN PATENT DOCUMENTS

| | | |
|---|---|---|
| JP | 2005-249421 A | 9/2005 |
| WO | 03/019139 A3 | 3/2003 |
| WO | 03/071263 A1 | 8/2003 |
| WO | WO 2005/083119 A2 * | 9/2005 |

OTHER PUBLICATIONS

Micro-fluidic control by optically manipulated small particles, Tokyo University of Agriculture and Technology, Y. Shuhama, et al., 2005.

Design Consideration on Cassette-type Bio-MEMS with Actuators Toshiba Corporation, Corporate Research and Development Center, Yujiro Naruse, 2005.

Tohru, et al., MEMS, pp. 22-25, Nov. 2005.

Fabrication and design of open microchannels for capillary electrophoresis separations and matrix-assisted laser/desorption mass spectrometry analysis, Ken Tseng et al, SPIE vol. 3606, pp. 1-12, Jan. 1999.

Electrophoresis Separation in Open Microchannels. A Method for coupling Electrophoresis with MALDI-MS, Jun Liu et al, Analytical Chemistry, vol. 73, No. 9, May 1, 2001 pp. 1-6.

Capillary isoelectric focusing in pseudo-closed channel coupled to matrix assisted laser desorption/ionization mass spectrometry for protein analysis, Michelle L.S. Mok, et al, Royal Society of chemistry. pp. 1-2, 2004.

Creation of healthcare chip aiming at separation and analysis of whole blood, Y.Horiike, et al, H. Onoda School of Engineering, The University of Tokyo, Japan Soc. ME & BE, pp. 1-2, 2001.

High-Throughput and high-resolution two dimensional mapping of pI and m/z using biochip and MALDI TOF-MS NEC, NEC Fundamental and Environmental Res. Labs, Machiko Fujita et al., 2005.

* cited by examiner

[Fig.5]
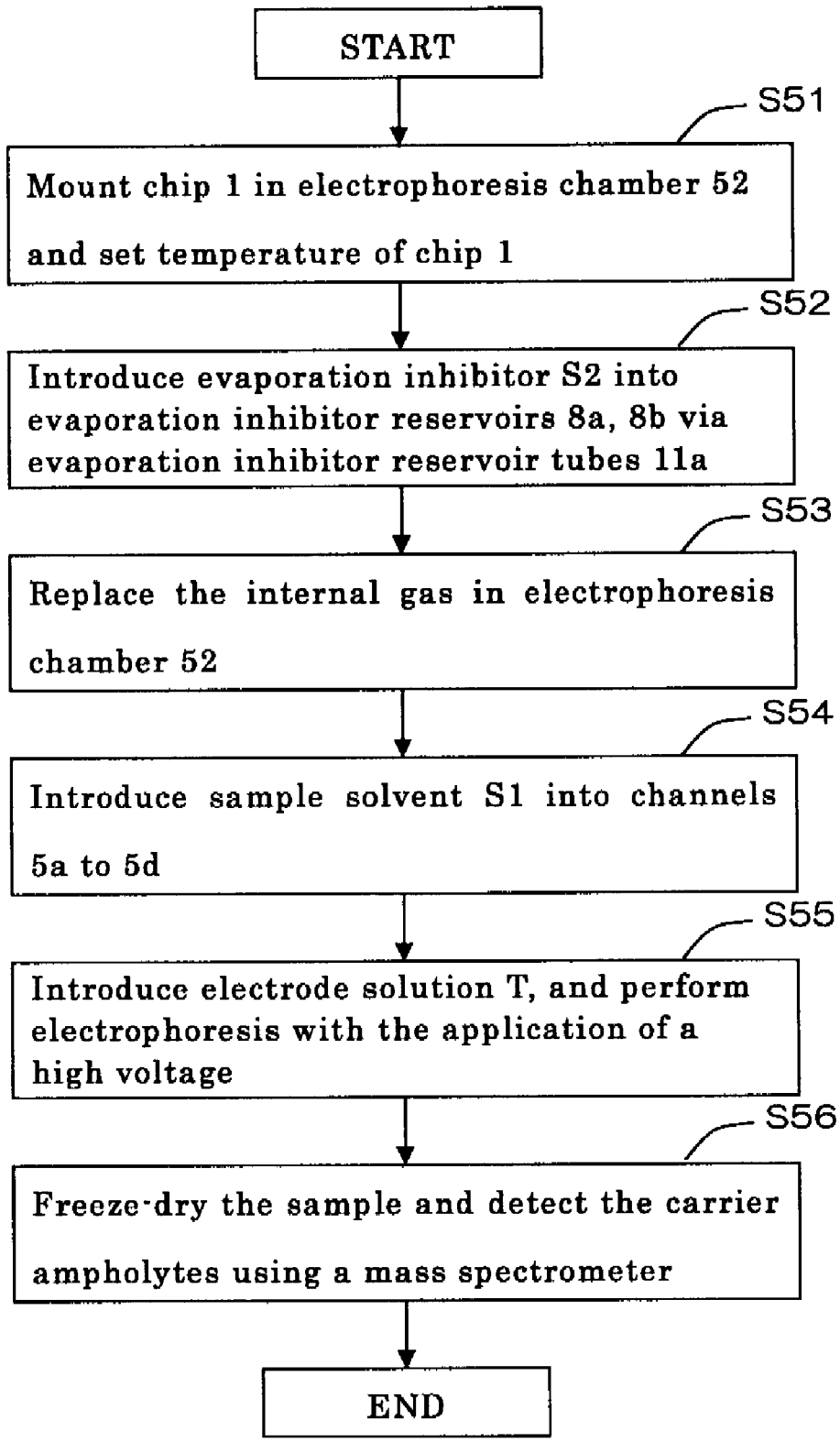

ELECTROPHORESIS CHIP, ELECTROPHORESIS APPARATUS, AND METHOD FOR ANALYZING A SAMPLE

TECHNICAL FIELD

The present invention relates to electrophoresis chip, electrophoresis apparatus using the same, and a method for analyzing a sample.

BACKGROUND ART

In recent years, developments in microelectro-mechanical system (MEMS) technology have spurred the development of novel systems to detect protein. According to a method, first, a sample solvent is introduced into a channel which is fabricated in a micro fluid chip. Next, protein that is contained in the sample solvent is fractionated by electrophoresis. The sample solvent is then dried in the channel, and a matrix for promoting ionization is added to the solvent. Subsequently, the protein fractionated in the channel is detected by means of a Matrix Assisted Laser Desorption/Ionization Mass Spectrometry (MALDI-MS).

According to Non-Patent Documents 1 to 3 and Patent Document 1, a sample that contains a matrix is fractionated using a groove-shaped channel formed in the chip having a non-sealed structure, i.e., a structure that is open at the top thereof. Then, the solvent in the channel is dried, and the fractionated sample is crystallized together with the matrix in the channel. Subsequently, the channel is scanned with a laser so that the fractionated sample is subjected to laser desorption and ionization, and is then subjected to mass spectrometry using the MALDI-MS.

In such an analyzing method, a sample is in a liquid state when protein is fractionated by electrophoresis and is in a dried state during the mass spectrometry. Therefore, a sample requires continuous treatment from a liquid state to a dried state in a single channel. According to Non-Patent Document 1, a solvent in a liquid sample is left as it is after electrophoresis in order to be dried. According to Non-Patent Document 2, a solvent in a liquid sample is dried by air blow supplied at a room temperature or dried in vacuum after fractionation of protein. According to Non-Patent Document 3, a solvent in a liquid sample is dried by heating a chip up to 60° C., or is dried in vacuum in a vacuum chamber. Patent Document 1 discloses an example in which a solvent in a liquid sample is transferred into a vacuum chamber so that it is freeze-dried.

[Non-Patent Document 1] Ken Tseng et al., "Fabrication and design of open microchannels for capillary electrophoresis separations and matrix-assisted laser/desorption mass spectrometry", Part of the SPIE Conference on Micro- and Nanofabricated Structures and Devices for Biomedical Environmental Applications 2, SPIE Vol. 3606 (1999), pp. 137-148

[Non-Patent Document 2] Jun Liu et al., "Electrophoresis separation in open microchannels. A method for coupling electrophoresis with MALDI-MS", Analytical Chemistry, Vol. 73 (2001), pp. 2147-2151

[Non-Patent Document 3] Michelle L. S. Mok et al., "Capillary isoelectric focusing in pseudo-closed channel coupled to matrix assisted laser desorption/ionization mass spectrometry for protein analysis", Analyst, Vol. 129 (2004), pp. 109-111

[Non-Patent Document 4] Yasuhiro Horiike et al., "Creation of Health Care Chip Aiming at Separation and Analysis of Trace Amount of Whole Blood", Medical Electronics and Bio Medical Engineering, Vol. 39, Special Edition 2 (2001), pp. 2 & 3

[Patent Document 1] WO03/071263

[Patent Document 2] Japanese Patent Laid-Open Publication No. 2002-310858

DISCLOSURE OF THE INVENTION

However, the above described related art has the following problems.

In the case of Non-Patent Document 1, in which a solvent is left as it is in order to be dried, drying requires too much time for the diffusion of the fractionated protein into the solvent, leading to a degraded fractionating performance. In addition, the solvent is not uniformly dried but is formed into liquid droplets in the process of drying the solvent. Since the droplets can move in a channel, the fractionated pattern of protein may be destroyed.

In the cases of Non-Patent Documents 2 and 3, a solvent is dried more quickly, and the dispersion of protein in the solvent is limited. However, similar problem occurs because a solvent is easily formed into liquid droplets, which easily move in a channel due to the air current that is generated in the drying process or in a vacuum exhaustion process. The disadvantageous movement of the droplets in a channel can not be solved by heat drying because the solvent is also formed into liquid droplets in this case.

Meanwhile, in the case of Patent Document 1, in which a chip is freeze-dried in a vacuum chamber, the above problem appears to be solved because neither movement of a sample nor diffusion of protein occurs after freeze-drying. However, this method actually requires much time to cool a chip after removing platinum electrodes and to put the chip in a vacuum chamber. The fractionated protein may be diffused in the solvent during these processes. Therefore, this method is not necessarily an effective solution.

An object of the present invention is to provide a technology which makes it possible to stably maintain a sample that contains protein under electrophoresis in a liquid state, to enable immediate freeze-drying of the sample after electrophoresis and then to stably maintain the sample in a dried state.

In order to achieve the above object, an electrophoresis chip of the present invention, comprises a substrate, a channel which is provided on a surface of the substrate and which has an opening at a top thereof, wherein a sample solvent is adapted to be supplied to the channel, and an evaporation inhibitor reservoir for storing an evaporation inhibitor for the sample solvent, the reservoir being provided independently of the channel and being spatially connected to the opening of the channel.

Thus, a sample solvent, which is introduced into the channel that is provided on the surface of the substrate, can be prevented from evaporating because the evaporation inhibitor is introduced into the evaporation inhibitor reservoir and the evaporation inhibitor evaporates. Since the evaporation inhibitor reservoir is provided independently of the channel, mixture of the sample solvent in the channel and the evaporation inhibitor in the evaporation inhibitor reservoir can be prevented.

The evaporation inhibitor reservoir is preferably provided on the surface of the substrate. A plurality of projections may be formed on a bottom of the channel.

An electrophoresis apparatus of the present invention includes an above described electrophoresis chip, an electrophoresis chamber for hermetically receiving the electrophoresis chip, and means for controlling temperature of the electrophoresis chip. The electrophoresis apparatus may include means for replacing internal gas in the electrophoresis chamber.

A method for analyzing a sample according to the present invention comprises a step of generating saturated vapor, a step of introducing the sample solvent, and a step of performing electrophoresis on the sample by applying a voltage to the channel.

In the step of generating saturated vapor, saturated vapor of an evaporation inhibitor is generated in a space that is adjacent to an opening of a channel, the channel being provided on a surface of a substrate, the evaporation inhibitor containing at least a constituent which is one of constituents of a sample solvent and which produces maximum partial pressure in saturated vapor pressure at a temperature at which electrophoresis is performed.

In the step of introducing the sample solvent, the sample solvent is introduced into the channel after the step of generating saturated vapor. The step of performing electrophoresis on the sample by applying a voltage to the channel is performed after the step of generating saturated vapor and the step of introducing the sample solvent.

Saturated vapor of an evaporation inhibitor containing at least a constituent which produces the maximum partial pressure of saturated vapor pressures at the temperature at which the electrophoresis is performed, among the constituents of a sample solvent which contains the sample, is produced, so that the evaporation of the constituent which produces the largest amount of evaporation in the sample solvent can be effectively prevented.

A method for analyzing the sample according to an exemplary embodiment sample of the present invention may further include a step of replacing a gas in the space adjacent to the opening of the channel with an inert gas, the step of replacing the gas being performed between the step of generating saturated vapor and the step of introducing the sample solvent.

The method for analyzing the sample may further include the step of freezing the sample on which the electrophoresis was performed, and the step of drying the frozen sample.

As explained above, according to the present invention, evaporation of a sample solvent can be effectively prevented. As a result, an electrophoresis method in which a sample is freeze-dried can be achieved without moving a chip after electrophoresis. In addition, the processes from electrophoresis to freeze-drying can be rapidly performed. Further, the dried state of the sample can be stably maintained.

BRIEF DESCRIPTION OF THE DRAWINGS

FIG. 5 is a flowchart showing a method for analyzing a sample according to an exemplary embodiment of the present invention.

Figure 1:
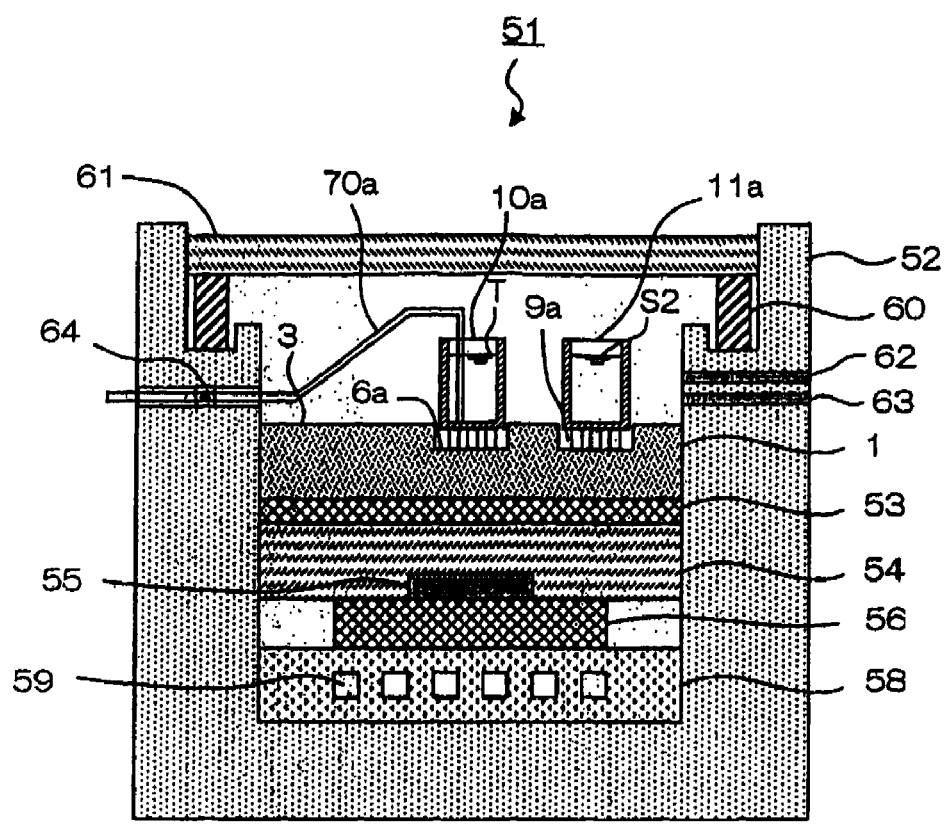
FIG. 1 is a schematic cross-sectional view showing an electrophoresis apparatus according to an exemplary embodiment of the present invention.

DESCRIPTION OF SYMBOLS 1 electrophoresis chip (chip)
2 substrate
3 surface
4a to 4d opening (open area)
5a to 5d channel
6a to 6h solvent supplying portion
8a, 8b evaporation inhibitor reservoir
9a, 9b evaporation inhibitor supplying portion
10a to 10h electrode solution reservoir tube
11a, 11b evaporation inhibitor reservoir tube
51 electrophoresis apparatus
52 electrophoresis chamber
53 thermally conductive gel sheet
54 support base
55 temperature sensor
56 Peltier device
58 cooling plate for liquid cooling
59 pipe
60 packing
61 glass lid
62 exhaust port
63 gas inlet port
70a to 70h electrode
S1 sample solvent
S2 evaporation inhibitor
T electrode solution

BEST MODE FOR CARRYING OUT THE INVENTION

Next, an exemplary embodiment of the present invention will be explained with reference to the drawings. FIG. 1 is a schematic cross-sectional view showing an electrophoresis apparatus according to an exemplary embodiment of the present invention. FIG. 2 is a schematic plan view showing an electrophoresis chip which is provided in the electrophoresis apparatus of FIG. 1.

Electrophoresis apparatus 51 is basically comprised of an electrophoresis chip (hereinafter, referred to as chip 1) and electrophoresis chamber 52 that can hermetically hold chip 1.

Chip 1 is fixed to support base 54 via thermally conductive gel sheet 53. Since a voltage of several KV is applied between electrodes during isoelectric focusing, support base 54 is preferably made of electrically insulating ceramics having high thermal conductivity, such as Shapal and Shapal M (trademark), which is made of aluminum nitride, in order to prevent a short circuit.

Temperature sensor 55 is mounted under support base 54. In order to accurately measure chip temperatures, it is desirable to mount temperature sensor 55 as close to chip 1 as possible, such as under chip 1. However, in order to prevent failure of temperature sensor 55 that can be caused by a short circuit induced by application of a high voltage, temperature sensor 55 is preferably mounted under support base 54 having high electrically insulating performance.

Peltier device 56, which is a temperature control means (cooling/heating mechanism) for controlling the temperature of chip 1, is disposed under support base 54. Peltier device 56 may be small-sized as long as it has a sufficient cooling and heating capacity. The in-plane uniformity of the temperature of chip 1 during cooling/heating can be ensured by using support base 54 formed of a material having a high thermal conductivity.

Cooling plate 58 for cooling a solution is disposed under Peltier device 56 in order to remove heat in Peltier device 56.

Pipes 59 for circulating coolant extend through the inside of cooling plate 58. The coolant, which is supplied from a chiller (not shown), can be circulated through pipes 59 to remove the heat. Therefore, cooling plate 58 is preferably formed of a material having high heat conductivity, such as aluminum or copper, and the surface thereof is preferably treated with oxidation in order to improve resistance against corrosion. The coolant may be water, Nybrine (trademark) or the like. The contact surface between cooling plate 58 and Peltier device 56 or the contact surface between Peltier device 56 and support base 54 is preferably coated with a paste to compensate for surface roughness and thereby to improve heat contact, such as heat transfer grease.

Electrophoresis chamber 52 is covered with glass lid 61 via packing 60, and a hermetically sealed space is formed within electrophoresis chamber 52. Electrophoresis chamber 52 is preferably made of a material having low thermal conductivity (high heat insulating properties), high electrically insulating properties, and high chemical resistance, such as a fluororesin.

Electrophoresis chamber 52 is provided with means for replacing internal gas, which is exhaust port 62 for exhausting internal gas in electrophoresis chamber 52, and gas inlet port 63 for introducing gas into electrophoresis chamber 52. Exhaust port 62 and gas inlet port 63 are preferably provided with valves (not shown) that are located in close vicinity of the ports outside electrophoresis chamber 52. This configuration allows electrophoresis chamber 52 to be insulated from the outside, and enables accurate control of the evaporation pressure in the hermetically sealed space.

Figure 2A:
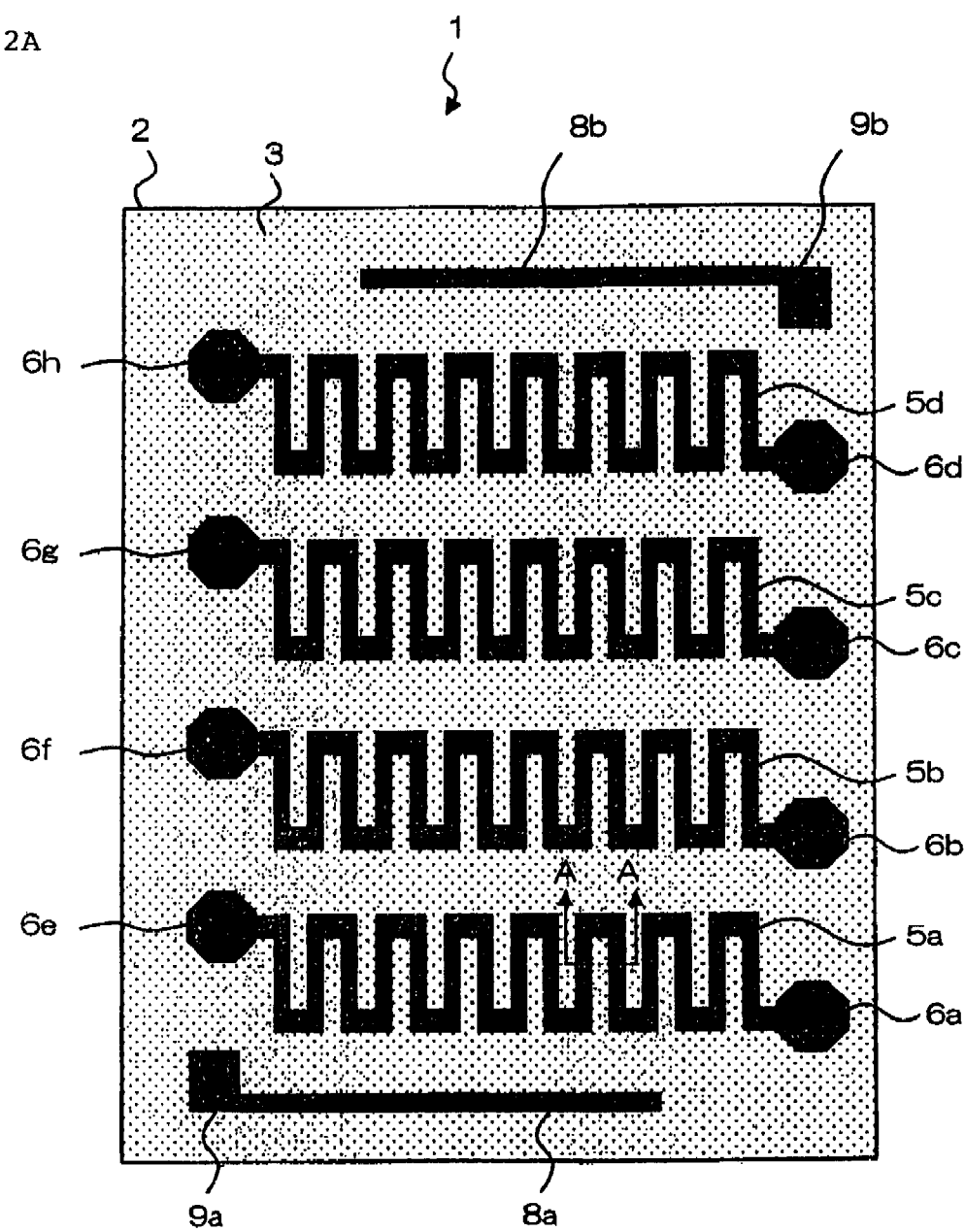
FIG. 2A is a schematic plan view showing an electrophoresis chip which is provided in the electrophoresis apparatus of FIG. 1.
Figure 2B:
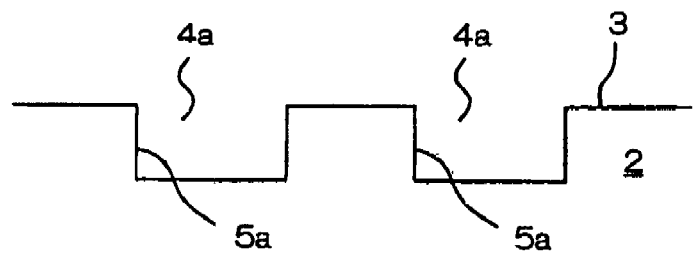
FIG. 2B is a cross-sectional view showing the electrophoresis chip cut along line A-A in FIG. 2A.

Referring to FIG. 2A, which is a plan view of a chip, and FIG. 2B, which is a cross-sectional view of the chip cut along line A-A in FIG. 2A, chip 1 includes substrate 2. Substrate 2 is fabricated by processing an insulating substrate made of quartz glass in order to enable electrophoresis, but may be made of any other materials, such as plastic, as long as they provide insulation without causing influence on electrophoresis.

Substrate 2 is provided with channels 5a to 5d for electrophoresis on surface 3 thereof. Sample solvent S1 is supplied into channels 5a to 5d. Channels 5a to 5d have many bends to ensure a sufficient flow length, and have openings (open area) 4a to 4d which are open at the tops thereof (only opening 4a is shown in FIG. 2B). Both ends of channel 5a to 5d are connected to solvent supplying portions 6a to 6h, which function as sample inlet ports to supply sample solvent S1 into channels 5a to 5d. Since solvent supplying portions 6a to 6h are provided on both ends of channels 5a to 5d, and thereby the sample inlet ports are provided on both ends of channels 5a to 5d, a sample can be introduced in a shorter time as compared with a case in which the solvent supplying portion is only disposed at one end of each channel.

Solvent supplying portions 6a to 6h are also used to reserve electrode solution T. Electrode solution reservoir tubes 10a to 10h (only tube 10a is shown in FIG. 1), which are made of glass, are fixed by means of a fixing plate (not shown), as shown in FIG. 1. Solvent supplying portions 6a to 6h, which have more than one function as described above, have a slightly larger size than evaporation inhibitor supplying portions 9a, 9b, which will be explained later.

Referring to FIG. 1, electrode solution reservoir tubes 10a to 10h have platinum electrodes 70a to 70h which are fixed therein (only electrode 70a is shown in FIG. 1), respectively. Electrodes 70a to 70h can be fixed in various ways, but they are inserted into electrode solution reservoir tubes 10a to 10h via electrophoresis chamber 52 in the present exemplary embodiment. In order to seal electrophoresis chamber 52, the insertion hole that is formed in electrophoresis chamber 52 is preferably filled with sealant 64.

Figure 3:
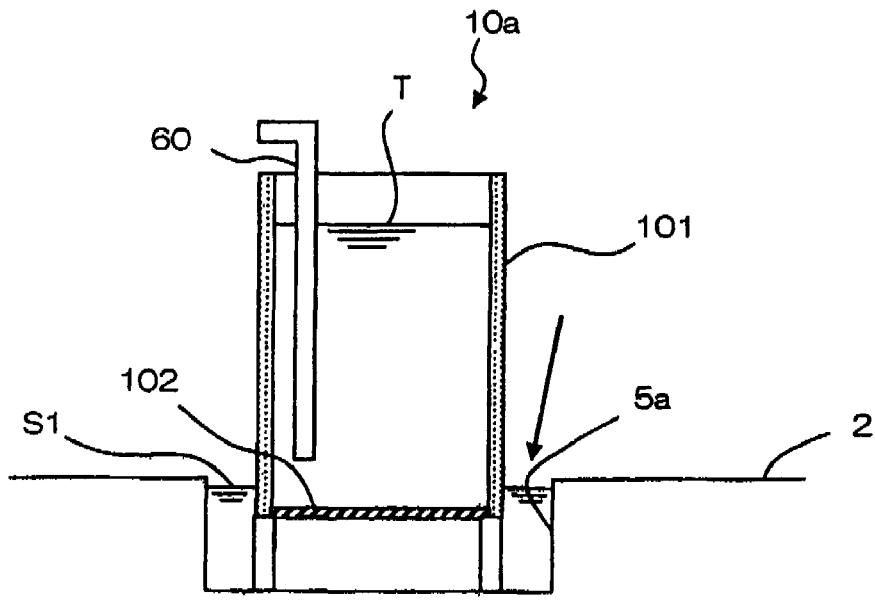
FIG. 3 is a side cross-sectional view of an electrode solution reservoir tube.

FIG. 3 is a side cross-sectional view of an electrode solution reservoir tube. Electrode solution reservoir tubes 10a to 10h include glass tube 101 and filter paper 102 that is formed of a hydrophilic PVDF film and that is attached to the glass tube by means of a chemically resistive epoxy adhesive. Filter paper 102 prevents electrode solution T from entering into channels 5a to 5d, and thereby increases the stability of isoelectric focusing, which is the most typical capillary electrophoresis. Moreover, in order to form a stable concentration gradient of hydrogen ions during isoelectric focusing, filter paper 102 is preferably impregnated with polyacrylamide gel for immobilizing pH which forms a desired hydrogen ion concentration. This enhances the reproducibility of a pH gradient that is formed in channels 5a to 5d.

Referring again to FIG. 2, substrate 2 has evaporation inhibitor reservoirs 8a, 8b to reserve evaporation inhibitor S2 on surface 3. Evaporation inhibitor S2 is supplied in order to prevent the evaporation of sample solvent S1. Evaporation inhibitor reservoirs 8a, 8b are provided independently of channels 5a to 5d, but are spatially connected to openings 4a to 4d of channels 5a to 5d. Evaporation inhibitor reservoirs 8a, 8b have evaporation inhibitor supplying portions 9a, 9b, respectively, at one end thereof.

Referring to FIG. 1, evaporation inhibitor supplying portions 9a, 9b have evaporation inhibitor reservoir tubes 11a, 11b that are made of glass and fixed thereto (only tube 11a is shown in FIG. 1). Evaporation inhibitor reservoir tubes 11a, 11b are fixed by means of fixing plates (not shown) that are provided in electrophoresis chamber 52. Evaporation inhibitor S2 is dripped on evaporation inhibitor supplying portions 9a, 9b via evaporation inhibitor reservoir tubes 11a, 11b, and spreads along elongated evaporation inhibitor reservoirs 8a, 8b so that the vapor of evaporation inhibitor S2 is produced from the entire area of evaporation inhibitor supplying portions 9a, 9b and evaporation inhibitor reservoirs 8a, 8b. Evaporation inhibitor reservoirs 8a, 8b are provided for the purpose of increasing the surface area of reservoirs as much as possible and of facilitating production of vapor.

Figure 4:
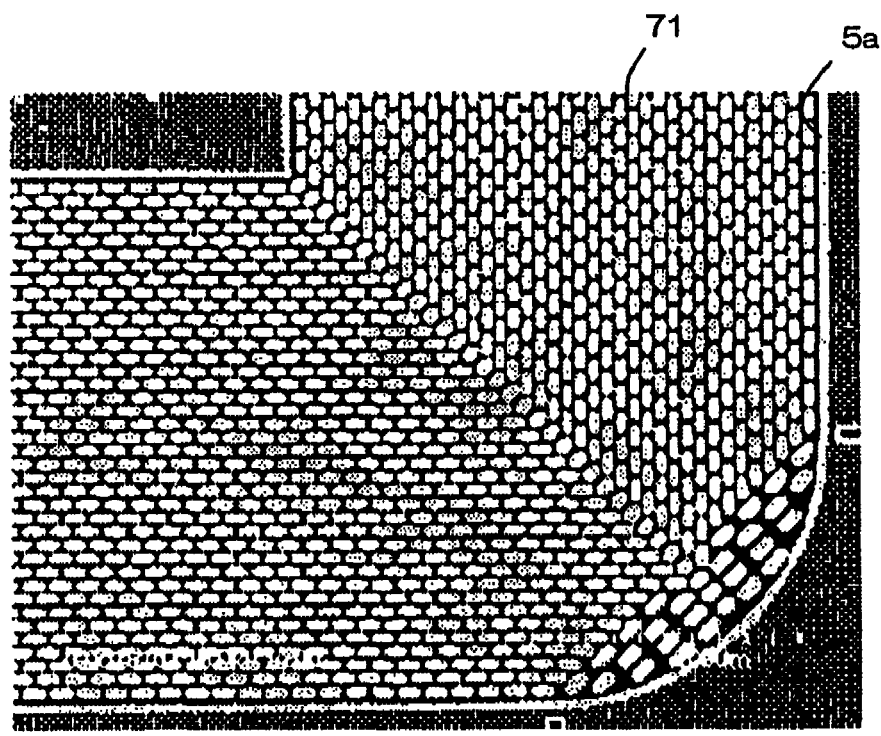
FIG. 4 is a partial plan view of a channel.

FIG. 4 is a partial plan view of the channel. Channels 5a to 5d have many projections 71 which are regularly arranged on the bottom thereof. Similar projections are provided on the bottom of solvent supplying portions 6a to 6h (under filter paper 102). Such an uneven structure enhances ability to hold solution, i.e., apparent lyophilic property, as compared with a case in which channels 5a to 5d and solvent supplying portions 6a to 6h have flat surfaces. Therefore, liquid that contains a sample can be stably held in channels 5a to 5d even if channels 5a to 5d only have a depth of about 10 μm. In addition, chip 1 of the present exemplary embodiment is configured such that heat exchanges occurs between chip 1 and a solution, which is introduced into channels 5a to 5d, via the uneven surface structure. Therefore, the temperature rise of the sample in channels 5a to 5d during electrophoresis, which is caused by Joule heat, can be mitigated, and stable performance of electrophoresis can be achieved.

According to Non-Patent Document 1, the channel has cross sections of a depth of 500 μm×a width of 500 μm, and a depth of 250 μm×a width of 250 μm. According to Non-Patent Document 2, the channel has a depth of 250 μm or 200 μm, and a width of 250 μm or 150 μm. According to Non-Patent Document 3, a channel is formed by pressing a platinum line having a diameter of 0.007 inch (about 180 μm) against a plastic substrate. According to Patent Document 1, a channel is formed by pressing platinum lines having a diameter of 0.005 inch (about 130 μm) and 0.007 inch (about 180 μm)

against a plastic substrate. By the way, MALDI-MS is known for high sensitivity of the order of amol to 10 fmol. Therefore, preparation of a sample used in MALDI-MS originally does not require a channel having a large cross sectional area as described above. Also, the width in the structures described above is larger than a diameter of a capillary used in capillary electrophoresis that is usually considered to be advantageous in heat dissipating performance, which is 100 µm or less.

However, a reduction in the cross sectional area of the channel described above does not lead to a stable introduction of a sample solvent into a channel, because the solvent in the channel is easily dried in an ordinary room. The same applies when the solvent is only subjected to temperature control using water cooling, which is described in Non-Patent Document 1. In particular, when MALDI-MS, which uses a laser having a diameter of about 100 µm, is applied, there is a possibility of a reduction in the effective laser irradiation area and of a resultant reduction in the efficiency if a channel diameter is reduced to be less than that value.

It might be effective to reduce the depth of a channel in order to reduce the cross sectional area of the channel. In this case, a certain width of the channel can be ensured, but a reduction in the depth of the channel increases the surface area through which the solvent evaporates relative to the volume of the channel. As a result, the solvent is more easily dried. Moreover, a reduction in the depth of a channel makes it difficult to hold a solution in the channel by gravity alone, and causes the possibility that a sample solvent will pour out of the channel. It is also difficult to hold the solution in the channel even if the length of a channel is increased in order to improve fractionating performance while keeping the volume of a sample solvent constant, because the surface area through which the solvent evaporates is increased.

However, by regularly arranging many projections 71 on the bottom of the channel, it is possible to stably hold the solution even in a channel having a width of 400 µm and a depth of 10 µm. Furthermore, these many projections significantly improve heat-dissipating performance and prevent the sample from drying during electrophoresis, which is caused by a temperature rise via Joule heat.

Next, a method for analyzing a sample that uses the electrophoresis chip and the electrophoresis apparatus described above will be explained with reference to the flowchart of FIG. 5.

(Step S51) First, as shown in FIG. 1, chip 1 is mounted in electrophoresis chamber 52. Then, coolant is circulated through pipes 59 by means of a chiller in order to set cooling plate 58 at a desired temperature. Next, Peltier device 56 is connected to a temperature controller for operation, and temperature sensor 55 is set at a predetermined temperature. The chip temperature is set at a desired temperature, for example, at 10° C., which is a typical temperature for isoelectric focusing. Heat in Peltier device 56 is removed to the outside via cooling plate 58.

(Step S52) Next, evaporation inhibitor S2 is introduced into evaporation inhibitor supplying portions 9a, 9b and evaporation inhibitor reservoirs 8a, 8b via evaporation inhibitor reservoir tubes 11a, 11b. Evaporation inhibitor S2 evaporates at a saturated vapor pressure that corresponds to the temperature in electrophoresis chamber 52, and the saturated vapor of evaporation inhibitor S2 is generated in electrophoresis chamber 52 including the space adjacent to openings 4a to 4d of channels 5a to 5d.

In the present exemplary embodiment, evaporation inhibitor reservoirs 8a, 8b are provided on chip 1. This configuration may be improper for accurate humidity control, for example, in a manner in which as much high humidity as possible is achieved without causing dew condensation on chip 1. However, this configuration is advantageous in that it facilitates ease of use by arranging the vapor source, which easily becomes dirty and requires complicated maintenance, on a chip and by treating the vapor source as a dispensable component. Also, it is easy for this configuration to form a sealed structure for vacuum exhaustion because there is no need to introduce or remove a solution after attaching a glass lid. A number of methods that use the capillary are described, for example, in Non-Patent Document 3 and Patent Document 2 had been proposed before Patent Document 1 was disclosed. However, it is significantly difficult for a sealed structure, which will enable vacuum exhaustion, to be formed based on these methods. Further, salt bridges, which have been generally used in capillary isoelectric focusing, as disclosed in Non-Patent Document 3 and Patent Document 2 and so on, and which also have been used in chip technology, as described in Non-Patent Document 4, are disadvantageous in strength because no consideration has been given about how to use the salt bridges while allowing vacuum exhaustion. Therefore, it is difficult to freeze dry a sample in an electrophoresis chamber immediately after electrophoresis is completed, as achieved in the present exemplary embodiment.

Evaporation inhibitor S2 may be the same as sample solvent S1, or may be any solvent that contains a constituent that forms a major element (a major partial pressure ratio) of vapor that is generated by sample solvent S1 at the temperature for the electrophoresis. For example, when isoelectric focusing is performed at a temperature of 10° C., a solvent made of a mixture of ethylene glycol and pure water with a volume ratio of 2:8 is often used, and the vapor pressure of pure water at 10° C. is about five hundred times as high as that of ethylene glycol. Therefore, in this case, evaporation inhibitor S2 may be a mixture of ethylene glycol and pure water, but also may be pure water alone having a high vapor pressure. Unlike gel electrophoresis, capillary electrophoresis, which is performed on a chip of the present exemplary embodiment and which is completed in a period of time no longer than few hours, only requires that the content of a solvent does not significantly change. Therefore, it is not necessarily that evaporation inhibitor S2 strictly corresponds to sample solvent S1. However, evaporation inhibitor S2 preferably contains at least a constituent (pure water in the above case) which is one of the constituents of sample solvent S1 and which produces the maximum partial pressure in the saturated vapor pressure at the temperature at which electrophoresis is performed.

(Step S53) After formation of a sealed structure, an inert gas, such as nitrogen gas, is fed from gas inlet port 63, and the internal gas in the chamber is exhausted through exhaust port 62 so that the internal gas in electrophoresis chamber 52 is replaced. This limits any adverse effect on the formation of a concentration gradient of hydrogen ions which is caused by dissolution of carbon dioxide in the air into sample solvent S1 and electrode solution T. Gas replacement can be achieved without causing any change in humidity by replacing the gas at a rate which is sufficiently smaller than the evaporation rate of evaporation inhibitor S2 at which evaporation inhibitor S2 evaporates from evaporation inhibitor reservoir tubes 11a, 11b.

Evaporation inhibitor reservoir tubes 11a, 11b ensures constant humidity control as compared with a case in which such a lid that is described in Non-Patent Document 3 and Patent Document 1 is used. Specifically, in the technology described in Non-Patent Document 3 and Patent Document 1, saturation of vapor pressure in the space under the lid requires evaporation of the solvent in channels. In this case, a volume of about 1 microliter of the solvent is required for evaporation, although it depends on the space under the lid. Since the volume of solution in a channel is on the order of microliter, the amount of evaporation is not negligible, and may lead to difficulty in keeping both the humidity and the concentration of the sample solvent at a constant level simultaneously. On the contrary, in the present exemplary embodiment, evaporation inhibitor reservoir tubes 11a, 11b are provided independently of channels 5a to 5d, and accordingly, it is possible to keep both the humidity and the concentration at a constant level simultaneously.

(Step S54) Next, when the humidity in electrophoresis chamber 52a becomes sufficiently high, sample solvent S1, which contains carrier ampholytes, such as peptide, polypeptide or protein which are fractionated according to their isoelectric points, and which contains other ampholytes, is first introduced into channels 5a to 5d by dripping the solvent with a pipet (see the arrow in FIG. 3). After dripping sample solvent S1, channels 5a to 5d are rapidly filled with sample solvent S1. Dried filter paper 102 that is impregnated with polyacrylamide gel for immobilizing pH absorbs the solvent so that filter paper 102 is ready to operate as a salt bridge.

(Step S55) In this state, an acid or alkali electrode solution T is introduced into each one of electrode solution reservoir tubes 10a to 10h. Electrode solution T is prevented from entering into channels 5a to 5d by filter paper 102. Moreover, a fine pH reproducibility which electrolyte T lacks is supplemented, and the concentration of the hydrogen ions can be achieved on both ends of the channel with a high reproducibility owing to the effect of the gel for immobilizing pH. Accordingly, the concentration gradient of the hydrogen ion which is formed by an application of a voltage can be stabilized.

Then, glass lid 61 is mounted to seal electrophoresis chamber 52, and at the same time a high voltage is applied between each pair of electrodes 70a to 70h, which are inserted in electrode solution reservoir tubes 10a to 10h, with the positive pole corresponding to acid and with the negative pole corresponding to alkali, so that a concentration gradient of hydrogen ions is formed and the carrier ampholytes are fractionated (electrophoresis).

(Step S56) Subsequently, Peltier device 56 is used to freeze the fractionated solvent. After freezing, vacuum exhaustion through exhaust port 62 and freeze-drying are conducted so that the carrier ampholytes can be dried without disturbing the fractionated patterns. Then, an ionization promoter is added by spraying or by means of a dispenser, as needed, and the carrier ampholytes are detected using a mass spectrometer.

As explained above, according to the present invention, evaporation of a sample solvent can be limited by forming saturated vapor of an evaporation inhibitor in the space adjacent to the opening of channels that are provided on the surface of the substrate, wherein the evaporation inhibitor is the same as the sample solvent or contains at least a constituent that produces the maximum saturated vapor pressure at a temperature at which electrophoresis is performed. Therefore, the liquid state of a sample that is fractionated by electrophoresis on a chip can be stably maintained, and the movement of the sample can be prevented. Accordingly, the fractionating performance can be improved.

Moreover, since the electrophoresis chamber is hermetically sealed, the temperature, humidity and pressure in the electrophoresis chamber can be controlled independently of exterior environment. For example, the mechanism for exhausting and replacing gas in the electrophoresis chamber enables removal of carbonic acid gas in the atmosphere, which causes a problem in isoelectric focusing, and allows the chamber to be filled with an inert gas instead of the carbonic acid gas. Furthermore, due to the mechanism for controlling chip temperature, a sample that is fractionated by electrophoresis on a chip can be frozen as it is after fractionating. Subsequent vacuum exhaustion of the chamber further enables freeze-drying. Alternatively, freeze-drying may be achieved by circulating dried gas. In this way, the electrophoresis method in which a sample is freeze-dried can be achieved without the need to move the chip after electrophoresis has been completed. In addition, the processes from electrophoresis to freeze-drying can be rapidly performed, and then the dried state of the sample can be stably maintained.

The dried state of the sample can be stably maintained without the possibility of dew condensation by raising the temperature to room temperature after freezing while the inside of the chamber is kept in a vacuum-exhausted state or while the chamber is filled with a dried gas.

As described above, according to the present invention, it is possible to stably maintain a sample that contains protein under electrophoresis in a liquid state, to enable immediate freeze-drying of the sample and then to stably maintain the sample in a dried state.

The invention claimed is:

1. An electrophoresis chip, comprising:
   a substrate;
   a channel which is provided on a surface of the substrate and which has an opening at a top thereof, wherein a sample solvent is adapted to be supplied to the channel;
   an evaporation inhibitor reservoir provided independently of the channel and being spatially connected to the opening of the channel; and
   an evaporation inhibitor for the sample solvent disposed in the evaporation inhibitor reservoir.

2. The electrophoresis chip according to claim 1, wherein the evaporation inhibitor reservoir is provided on the surface of the substrate.

3. The electrophoresis chip according to claim 1, wherein a plurality of projections are formed on a bottom of the channel.

4. An electrophoresis apparatus, comprising:
   the electrophoresis chip according to claim 1;
   an electrophoresis chamber for hermetically receiving the electrophoresis chip; and
   a Peltier device and a cooling plate for controlling temperature of the electrophoresis chip.

5. The electrophoresis apparatus according to claim 4, further comprising an exhaust port and a gas inlet port for replacing internal gas in the electrophoresis chamber, the exhaust port and the gas inlet port being formed on the electrophoresis chamber.

6. A method for analyzing a sample, comprising:
   a step of generating saturated vapor of an evaporation inhibitor in a space that is adjacent to an opening of a channel, the channel being provided on a surface of a substrate, the evaporation inhibitor containing at least a constituent which is one of constituents of a sample solvent and which produces maximum partial pressure in saturated vapor pressure at a temperature at which electrophoresis is performed;
   a step of introducing the sample solvent into the channel, the step of introducing the sample being performed after the step of generating saturated vapor; and a step of performing electrophoresis on the sample by applying a voltage to the channel, the step of performing electrophoresis being performed after the step of generating saturated vapor and the step of introducing the sample solvent.

7. The method for analyzing the sample according to claim 6, further comprising:
a step of replacing a gas in the space adjacent to the opening of the channel with an inert gas, the step of replacing the gas being performed between the step of generating saturated vapor and the step of introducing the sample solvent.

8. The method for analyzing the sample according to claim 6, further comprising: a step of freezing the sample on which the electrophoresis was performed; and a step of drying the frozen sample.

9. An electrophoresis chip, comprising:
a substrate;
a channel which is provided on a surface of the substrate and which has an opening at a top thereof, wherein a sample solvent is adapted to be supplied to the channel; and
an electrode disposed at each end of the channel for applying a voltage between each electrode;
an evaporation inhibitor reservoir for storing an evaporation inhibitor for the sample solvent, the reservoir being provided independently of the channel and being spatially connected to the opening of the channel,
wherein no electrodes are disposed at the evaporation inhibitor reservoir,
an evaporation inhibitor for the sample solvent disposed in the evaporation inhibitor reservoir.

* * * * *